United States Patent [19]

Murray et al.

[11] 4,224,697

[45] Sep. 30, 1980

[54] CONSTRAINED PROSTHETIC KNEE

[75] Inventors: Ian Murray, Bellevue, Wash.; Stanley Kampner, San Francisco, Calif.

[73] Assignee: Hexcel Corporation, San Francisco, Calif.

[21] Appl. No.: 940,526

[22] Filed: Sep. 8, 1978

[51] Int. Cl.³ .............................................. A61F 1/03
[52] U.S. Cl. ................................. 3/1.911; 128/92 C
[58] Field of Search ..................... 3/1.9, 1.91, 1.911; 128/92 C

[56] References Cited

U.S. PATENT DOCUMENTS

| | | | |
|---|---|---|---|
| 3,760,427 | 9/1973 | Schultz | 128/92 C X |
| 3,824,630 | 7/1974 | Johnston | 3/1.911 |
| 3,869,729 | 3/1975 | Attenborough | 128/92 C X |
| 4,016,606 | 4/1977 | Murray et al. | 128/92 C X |
| 4,081,866 | 4/1978 | Upshaw et al. | 128/92 C X |
| 4,085,466 | 4/1978 | Goodfellow et al. | 3/1.91 |

Primary Examiner—Clifford D. Crowder
Attorney, Agent, or Firm—Townsend and Townsend

[57] ABSTRACT

A constrained prosthetic knee having as its component parts a femoral implant, a tibial implant, and a meniscal plate disposed between the implants. Knee flexion and extension is permitted by compoundly curved condyle surfaces of the femoral implant, which resemble corresponding surfaces of a natural knee, and correspondingly shaped convex bearing surfaces in the meniscal plate and tibial implant. This interface is defined by a continuous, concave, spherically shaped surface in the upwardly facing plateau of the tibial implant and a corresponding, continuous, convex spherical surface of the meniscal plate. A post projects from the tibial implant into a cavity defined by the femoral implant and the free end of the post and the cavity have opposing, cooperating and overlapping ledges which maintain the implants constrained to each other. The ledges permit unrestrained flexion, extension and torsional movement of the knee and limited lateral rocking (adduction-abduction).

52 Claims, 9 Drawing Figures

CONSTRAINED PROSTHETIC KNEE

BACKGROUND OF THE INVENTION

This invention relates to an artificial knee prosthesis, or a prosthetic knee, for the replacement of a natural knee through surgical implantation.

In general, a natural knee is formed by the two condyles of the bottom part of the femur, the lower surfaces of which bear upon the complementarily shaped upper surface plateaus of the tibia through the intermediary of meniscii, a fibro-cartilage. Connection through the knee is provided by means of ligaments which also provide joint stability and help to absorb stresses applied to the knee. The femur, meniscii and tibia are normally subjected to relatively large forces in the course of supporting the major portion of a person's body weight.

Movement of the normal knee is complex, that is it is not simply a pivotal or rotational movement. Rather, a healthy, natural knee has the ability to move in four distinct manners. First, the natural knee joint permits flexion and extension between the femur and the tibia through an arc of about 135°. This motion is a combined rotational, rocking and gliding movement of successive points of the femoral condyles and the tibial plateaus. Secondly, the healthy, natural knee permits a relative rotational movement between the condyles and the tibial plateaus. Thirdly, the knee permits some limited relatively sliding motion (in conjunction with other knee motions) which might be described as taking place in a generally horizontal plane between the condyles and the plateau; and fourthly the knee permits a rolling-type motion, frequently referred to as abduction and adduction, between the condyles and the plateaus which might best be described as a limited rocking-type motion in a lateral direction, that is generally perpendicular to the plane in which the knee most commonly articulates (flexion and extension).

Aside from the proper geometric configuration of the condyles and the tibial plateaus, an effective, free movement of a natural knee in these four directions requires the presence of a fibro-cartilage, commonly referred to as meniscus, between the condyles and the plateaus. When the meniscii become damaged, deceased or inflammed, they cease to function properly, the mobility of the knee joint becomes increasingly impaired and movements are accompanied by increasingly severe pains.

To alleviate this condition, it is sometimes necessary to replace the natural knee by surgically implanting a prosthetic knee.

Review of the Prior Art

The prior art is replete with a great variety of prosthetic knees. In all instances, the prior art seeks to approximate the mobility of a natural knee to a greater or lesser extent by providing artificial substitutes for the condyle surfaces, the condyles as a whole, the entire lower portion of the femur, the tibial plateau or the entire upper portion of the tibia, including the plateau. The following U.S. patents disclose a variety of differently constructed and operating prosthetic knees:

U.S. Pat. No. 3,715,763;
U.S. Pat. No. 3,774,244;
U.S. Pat. No. 3,813,700;
U.S. Pat. No. 3,824,630;
U.S. Pat. No. 3,852,830;
U.S. Pat. No. 3,924,277;
U.S. Pat. No. 3,964,106;
U.S. Pat. No. 4,000,525;
U.S. Pat. No. 4,034,418.

Further, the article "The Surgical Replacement of the Human Knee Joint" by D. A. Sonstegard, L. S. Matthews and H. Kaufer, published in the January 1978 issue (Vol. 238, No. 1) of Scientific American on pages 44-51, gives a good summary of the problems encountered with prosthetic knees and discusses the current state of the art in general terms.

There are two main types of prosthetic knees. The first type is an articulated device which provides a constraining mechanical linkage between the femoral and tibial implants; that is one in which the two implants are mechanically constrained to each other by means of a hinge, a ball and socket type joint, etc.

The second type of prosthetic knee is a non-constrained or unlinked device. In these devices, the emphasis is on replacing some or all of worn and/or deceased load bearing surfaces of the knee. They do not include a mechanical link, hinge, or similar constraint between the femoral and tibial implants. Instead, the stability of the prosthetic knee is primarily provided by the patient's ligaments and muscles.

The present invention relates to knees of the former type, namely constrained prosthetic knees.

Generally speaking, the replacement of an entire natural knee requires the surgical implantation of the prosthetic knee by removing at least portions of the femoral condyles and the tibial plateaus and implanting therein normally metallic substitutes referred herein as "femoral implants" and "tibial implants".

Although the exact construction of the femoral and tibial implants of such prosthetic knees and the exact manner in which they are connected to the femur and the tibia, respectively, varies, they all have the common characteristic that the implants are placed against the femur and the tibia and secured thereto with a bonding agent or cement.

Clinical tests and experience have shown that prior art prosthetic knees eventually fail, often not because of a failure of their component parts but because of a failure of the bond between the implants and the bone structures. Applicants believe that the reason for this failure is the marked difference in the modulus of elasticity between the cement and the bone structure to which it bonds the implants. In other words, it appears that in prosthetic knee implants the weakest point is the cement-bone interface (hereinafter sometimes referred to as the "interface").

Upon detailed study and analysis, it appears to applicants that the failure of the cement-bone interface and the resulting loosening of the implants results primarily from tensile, shear and torsional stresses. On the other hand, studies have shown that compressive stresses which result from the load carried by the knee are better tolerated by the cement and the interface.

Tensional stresses might be the ones least tolerated by the interface and they can develop whenever the restricted mobility of a prosthetic knee or its geometry are such that either one or both of the implants are loaded so as to generate a bending moment at the interface, thereby stressing all or at least part of the interface in tension. Typically, this occurs when the knee joint moves in either the first or the fourth direction discussed above.

Shear stresses at the interface can be developed due to restrictions in the mobility of the knee joint in the above discussed third direction (horizontal sliding) while torsional stresses are developed if there are restrictions in the mobility of the joint in the above discussed second direction, namely rotation.

Eventually it became apparent that the provision of a femoral implant and of a tibial implant alone could not adequately duplicate the motion freedom provided by the natural knee since the function performed by the meniscus in a natural knee is simply deleted. Generally speaking, that function can be defined as giving the joint a certain multidirectional mobility due to the resilient deformability of the meniscii between the relatively rigid femur and tibia.

To overcome this shortcoming, German Offenlegungsschrift No. 2,550,704 proposes an unrestrained prosthetic knee which includes as a third member disposed between the two implants a meniscal plate. This plate has a lower, flat surface that cooperates with a correspondingly flat surface of the tibia implant and an upper, concave, spherically shaped surface which receives a correspondingly shaped convex surface of the femoral implant. One set of implants is provided for each condyle-plateau pair so that a complete prosthetic knee constructed in accordance with the German publication comprises two sets of implants, each having an independent meniscal plate between them.

The incorporation of the meniscal plate suggested in the German publication, in fact, significantly enhances the mobility of such a prosthetic knee. Especially the provision of cooperating flat surfaces between the tibial implants and the meniscal plate enables relatively free rotational movements between the implants, thereby avoiding the transmission of corresponding forces between them. Instead, torsional forces between the femur and the tibia are transmitted via the appropriate ligaments.

A problem encountered with the construction disclosed in the German publication, however, results from the difficulty of maintaining the flat surfaces of the two tibial implants parallel. If the surfaces are not parallel, relative rotational movements cannot take place, or at least cannot readily take place without transmitting corresponding torsional forces to the implants and thus subjecting the interfaces to the tortional stresses which, as above discussed, is to be avoided to prevent a loosening of the implants. Such precise alignment, however, of two independent implants is a most difficult task and it is estimated that only very few orthopedic surgeons are able to assure proper, aligned implantations on a regular basis.

More significantly, the two sets of cooperating spherical surfaces between the femoral implants and the meniscal plates preclude a free-sliding motion between the implants in the above discussed fourth direction, namely abduction or adduction. Instead of permitting relative sliding motion between the implants or between one of the implants and the meniscal discs such motion in fact causes a tilting, thereby transmitting relatively large, eccentrically acting forces to the implants which in effect generate bending moments and thus subject at least portions of the bone-cement interfaces to tension stresses, the type of stresses least tolerated by the interfaces.

Thus, the improved prosthetic knee disclosed in the German publication does not eliminate the persistent problem of preventing a loosening of the implant and the ultimate failure of the knee. At best, it postpones it.

Although the prosthetic knee disclosed in the German publication has a number of functional advantages over other prior art prosthetic knees, it is not suited for use as a constrained knee, i.e. it can be implanted only if the patient's ligaments are essentially intact. Prior art constrained prosthetic knees do provide the necessary connection between the two implants so that they cannot move axially away from each. Accordingly, such knees can be used when the patient's ligaments are damaged or unuseable. However, these prosthetic knees have severe limitations in their mobility and are likely to fail at their cement-bone interface for the above discussed reasons.

The following is a list of relevent United States patents which disclose constrained knee prostheses:

U.S. Pat. No. 3,760,427;
U.S. Pat. No. 3,795,922;
U.S. Pat. No. 3,837,009;
U.S. Pat. No. 3,848,276;
U.S. Pat. No. 3,909,854;
U.S. Pat. No. 3,918,101;
U.S. Pat. No. 3,934,272;
U.S. Pat. No. 3,969,773;
U.S. Pat. No. 4,001,896.

Typically these patents disclose prosthetic knees in which the relative motions between the femoral and the tibial implants are pivotal motions about a fixed pivot axis oriented transversely to the flexion-extension plane of the knee. In some instances the motion path is more refined and intricate (as in U.S. Pat. No. 3,969,773, for example) and in others slight additional motions are permitted (as in U.S. Pat. No. 3,934,272). Generally speaking, however, constrained prosthetic knees give the patient a distinctly limited mobility as compared with natural knees. Moreover, the motions permitted by such prosthetic knees are relatively unnatural, that is they fail to closely duplicate the motions permitted by a natural knee. This in turn increases undesired torsion, shear and tension stresses at the cement interfaces between the implants and the supporting bones, thereby hastening the failure of the implants.

SUMMARY OF THE INVENTION

The present invention is directed to a constrained prosthetic knee which substantially reduces the formation and/or transmission of tension, torsion and/or shear stresses between the implants while it assures a substantial duplication of the movements permitted by a natural knee, subject to a partial reduction in the mobility of the prosthesis in some direction due to its constraining features. Consequently, the occurrence of undesirable stresses at the cement-bone interface between the implants and the supporting bone structures is limited while the mobility of the prosthetic knee approximates the mobility of a natural knee much more closely than was the case in the past. Thus, implants constructed in accordance with the present invention have a much lesser propensity to fail, and they are more comfortable for the patient as compared to prior art constrained prosthetic knees.

Generally speaking, the present invention accomplishes this by providing both a femoral and tibial implant and by placing a meniscal plate between opposing surfaces of the implants. The meniscal plate and the implants as such provide a substantially complete relative freedom of motion between them in the above discussed four movement directions. Connected to the implants are means for constraining the implants to each other, that is for preventing their separation in axial (parallel to the knee prosthesis in its fully extended position) or lateral directions while permitting unrestrained flexion-extension movements over the desired extent (typically over an arc of 135°) and similarly unrestrained torsional movements while relative lateral movements between the implants are limited.

As a result, except to the extent the constraining means actually restricts relative movement between the implants the prosthetic knee of the present invention is substantially incapable of either generating or transmitting forces that can stress the cement-bone interface in tension, shear or torsion. Thus, the danger of a loosening of the interface due to such stresses, which was common in the past, is greatly reduced. Consequently, the constraint prosthetic knee of the present invention assures a long if not permanent service life.

The meniscal plate of the prosthetic knee of the present invention has a downwardly facing surface (hereinafter sometimes referred to as "undersurface") which is convex and compoundly curved. It cooperates with a similarly shaped, concave surface of the tibial implant to permit a substantially unrestrained relative movement between the surfaces when they are in mutual contact. Thus, the undersurface is spherically curved, or substantially spherically curved and it is received within a correspondingly shaped, concave surface (hereinafter sometimes referred to as "plateau surface") of the tibial implant.

This engagement of the two surfaces provides a large surface area for the transmission of compressive forces between the implants. This surface area, due to its shape, also provides unrestrained mobility between the mensical plate and the tibial implant so that shear or torsional forces cannot be generated by or transmitted between them. Further, the continuous, spherical character of the surfaces is such that there is effectively no eccentric application of compressive forces between them and, consequently between the implants. Bending moments, acting especially at the cement-bone interfaces, as heretofore encountered with prior art prosthetic knees can, therefore, not develop and tensional forces and stresses caused by such bending moments are prevented.

The upwardly facing surface of the meniscal plate is defined by two sections which cooperate with two condyle surfaces of the femoral implant. The latter have a surface configuration which is essentially the same as that of the natural condyles. Thus, the condyle surfaces of the femoral implant are convexly shaped in a compound manner while the meniscal plate defines a pair of spaced apart, concave bearing surfaces for them. A section of the meniscal plate between the bearing surfaces engages a recess between the condyle surfaces of the femoral implant to prevent substantially all relative motions between them except for flexion and extension motions (in the first direction).

Thus, flexion-extension motions of the prosthetic knee of the present invention take place at cooperating surfaces between the femoral implant and the meniscal plate while all other relative motions take place along the cooperating spherically shaped surfaces of the meniscal plate and the tibial implant. The spherical surfaces effectively prevent the transmission of forces other than compressive forces. To a large extent the former are transmitted in much the same manner as they are transmitted in a natural knee, that is via soft tissue and muscles surrounding the knee.

The constraint between the implants is defined by inter-engaging surfaces formed on the femoral implant and the tibial implant which prevent the separation of the implants in an axial direction, which limit lateral movements between the implants in the fourth direction (adduction and abduction), and which further normally define the limits of relative flexion and extension motions between the implants.

For this purpose the femoral implant is provided with a housing positioned between the condyle sections of the implant and overlying the above discussed recess between the condyle sections. The housing defines an interior cavity which is elongated in a direction parallel to the plane in which flexion-extension movements take place. The cavity communicates through a slot or cutout that generally faces the tibial implant.

The tibial implant is provided with a preferably cylindrical post which protrudes from the plateau surface towards the femoral implant and which extends through the slot into the interior space of the housing. A free end of the post has an enlarged diameter head portion to define a rim surface which is perpendicular to the post and which faces the plateau surface. The housing defines ledges or holding surfaces disposed within the cavity and positioned and dimensioned to engage the rim surface of the post and thus retain the post to the housing, thereby constraining the implants to each other.

In the preferred embodiment of the invention, the enlarged head portion of the post has a generally hemispherical, convex shape and it intersects the rim surface. The enlarged head portion is cut back at one end so as to define sloping surface sections which are contiguous with the rim surface and which slope away therefrom so as to permit flexion-extension movements between the condyle surfaces of the femoral implant and the corresponding bearing surfaces of the meniscal plate without interference from an engagement between the ledges and the rim surface. Furthermore, the slot is dimensioned and shaped so as to define the limits of flexion-extension movements. Lastly, the width of the cutout is somewhat larger than the diameter of the post to permit a limited, rocking type motion between the implant in the fourth direction.

From the preceding it will be apparent that the prosthetic knee of the present invention allows full motion freedom in the first direction within the limit of the flexion and extension movements; it allows free, unrestrained rotational movements between the implants about the extended knee axis; and it provides limited rocking type movements between the implants in the fourth direction. In addition, the spacing between the plateau surface of the tibial implant and the rim surface on the retaining post is chosen to permit limited, i.e. 2-4 mm relative motions between the implants in an axial direction so that the meniscal plate can be spaced a like amount from the cooperating surfaces of the tibial and-/or femoral implants to effectively "expand" the knee in an axial direction. While in such an expanded state the knee exhibits limited mobility in the third direction (horizontal sliding). Normally, however, the patient's body weight firmly biases the implants and the meniscal plate into mutual engagement.

Consequently, while the prosthetic knee of the present invention is fully constrained and can be implanted in a patient with severely damaged or no ligaments, it provides maximum freedom of motion between the implant and limits the formation of tension, shear and torsion stresses at the interfaces.

Structurally, the femoral and tibial implants are both made of metal, preferably of a chromium-cobalt-molybdenum alloy while the interposed meniscal plate is preferably made of ultra high molecular weight polyethelene. The surfaces of the metal implants which cooperate with surfaces of the meniscal plate are mirror-polished to minimize friction between them.

The femoral implant has downwardly depending extensions which match the natural condyles of the femur and it is of a unitary construction so as to eliminate alignment problems when the surgical implant is made. A space between the condyle portions of the femoral implant (beneath the cavity defining housing) is recessed for receiving an intercondylar eminence or protuberance of the mensical plate.

Preferably, the surfaces of each metallic implant which come in contact with and which are cemented to bone structure have recesses, grooves, etc. to both facilitate the retention of cement during their implanting and to provide spaces into which bone may grow to mechanically interlock it with the implant and to provide a connection which is as secure as possible.

DESCRIPTION OF THE PREFERRED EMBODIMENTS

Referring to FIGS. 1A–D, a natural human knee 2 is generally illustrated. For simplicity, only the femur 4 and the tibia 6 are shown, the fibula, which extends generally parallel to the tibia is of no importance for an understanding of the working of a knee and is, therefore, not shown. At the lower end the femur terminates in a pair of side-by-side femoral condyles 8 which are received by dished in meniscii carried on an upper end of the tibia which defines a tibial plateau 12. A natural human knee also includes a patella which is not illustrated in FIGS. 1A–D.

Figures 1A, 1B, 1C, 1D, 2A, 2B:
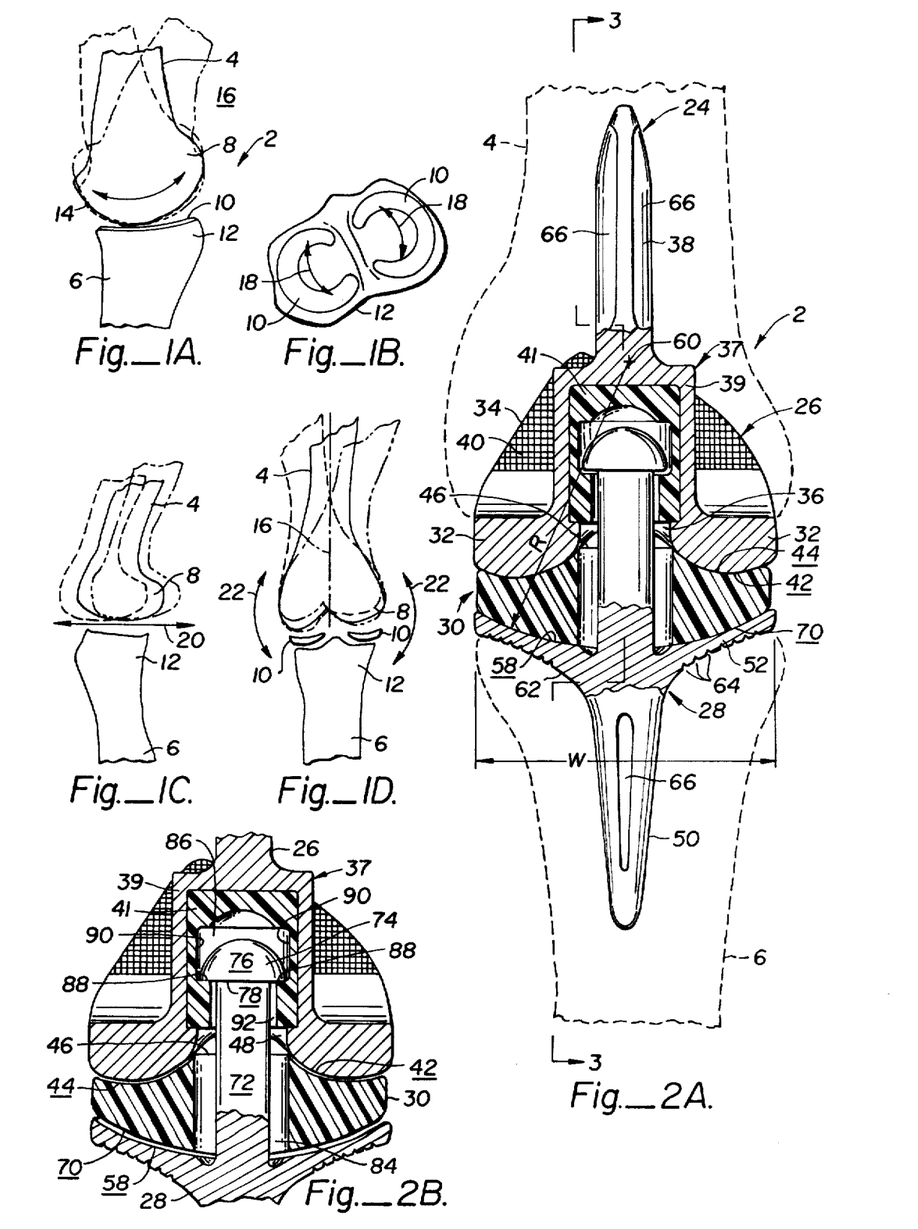
FIGS. 1A–D are schematic illustrations of motions permitted by a natural human knee.
FIGS. 2A and 2B are rear elevational views, in section, of a prosthetic knee constructed in accordance with the present invention and they illustrate the knee in its axially compressed and expanded state, respectively.

The perhaps most common and widely recognized motion of the knee is in flexion or extension and that motion is generally illustrated in FIG. 1A. The motion is a rocking type motion in the course of which downwardly facing, convex and compoundly curved surfaces 14 of the condyle slide and roll over an appropriately shaped, concave surface defined by each meniscus 10 and the tibial plateau 12. Flexion and extension of the knee joint takes places in the plane 16 in which FIG. 1A is drawn, also shown in FIG. 1D, which is generally vertical (when the patient stands in an upright position) and which is further generally parallel to the longitudinal extent of the condyle surfaces. Flexion and extension is thus a generally pivotal movement between the femur and the tibia although the movement does not take place about a single pivot axis but rather along a curved path defined by the condyle surfaces and the shape of the cooperating surfaces of the meniscii and the tibial plateau. For ease of reference this motion permitted by the natural knee is sometimes referred to as a motion in the "first direction".

FIG. 1B is a general plan view of the tibial plateau only, schematically illustrates the location and shape of natural meniscii 10, and the arrows 18 illustrate relative rotational motion permitted by knee joint 2 about a generally vertical axis (when the patient is in the upright position) over a limited arc defined by the cooperating surfaces of the condyles, meniscii and tibial plateau. For ease of reference this rotational motion permitted by the natural knee is sometimes referred to as a motion in the "second direction".

FIG. 1C illustrates another motion permitted by the natural knee, a very limited, relative sliding motion (which, in a knee is accompanied by a rolling motion) between the condyles and the tibial plateau in a plane substantially perpendicular to the fully extended tibia and femur, e.g. in a generally horizontal plane when the patient is standing. This relative sliding motion is illustrated in FIG. 1C by arrow 20 and is sometimes referred to as a motion in the "third direction".

FIG. 1D shows yet another motion permitted by the natural knee, namely a lateral sliding or rocking type motion illustrated by arrows 22. This motion, frequently called abduction and adduction, is sometimes referred to as a motion in the "fourth direction".

Referring now to all figures, a prosthetic knee 24 constructed in accordance with the present invention duplicates the functions of the natural knee, except for the constraining function incorporated in the prosthetic knee as is further discussed below. However, structurally the prosthetic knee differs from a natural knee in several important respects to take into account and alleviate the problems one is faced with when a prosthetic knee is implanted. In particular, and again disregarding the constraining function for the moment, the prosthetic knee of the present invention is shaped so that it substantially eliminates stresses other than compressive stresses at the cement-bone interface.

Prosthetic knee 24 generally comprises a femoral implant 26 which is secured to the patient's femur 4 as further described below; a tibial implant 28 secured to the upper end of the patient's tibia 6; and an intermediate meniscal plate 30. As is more fully described below it will be observed that the interface between the tibial implant and the meniscal plate is defined by cooperating spherically shaped, concave and convex surfaces, respectively, which enable sliding motions along these surfaces between the tibial implant and the meniscal plate and, thereby, between both implants. These free motion is not present on a natural knee; however, a natural knee is not confronted with the earlier discussed loosening problems between the implants and the bone structure at the cement-bone interface.

Figure 3:
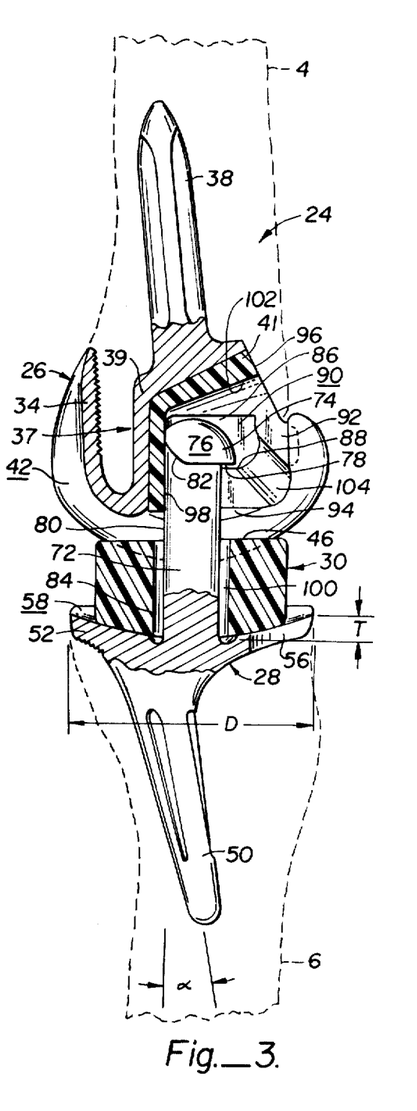
FIG. 3 is a side elevational view, in section, of the prosthetic knee shown in FIG. 2 and is taken on line 3—3 of FIG. 2A.
Figure 4:
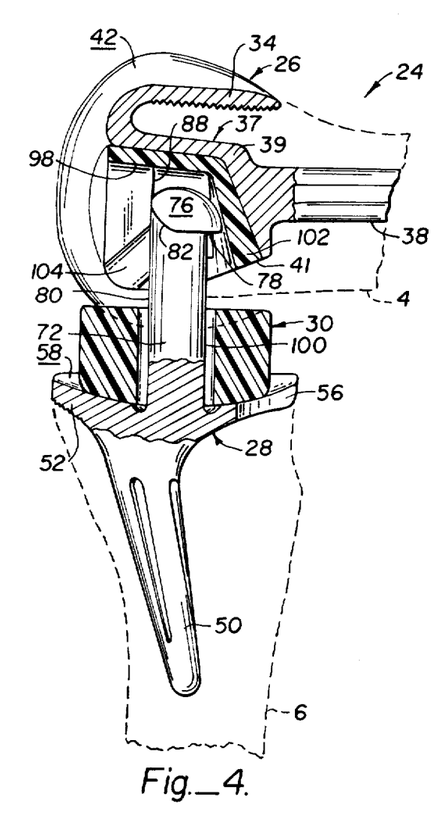
FIG. 4 is a side elevational view similar to FIG. 3 but illustrates the relative position of the components of the prosthetic knee in their fully flexed positions.
Figure 5:
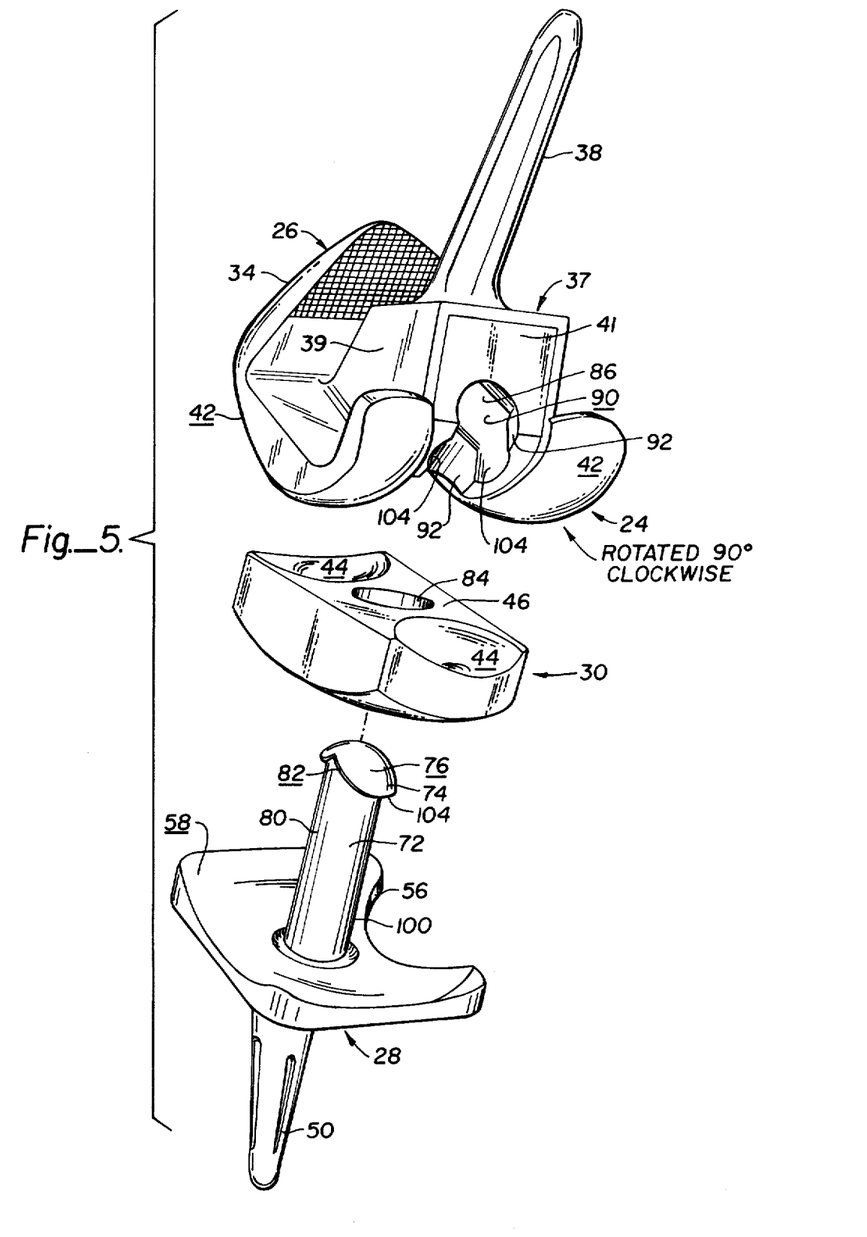
FIG. 5 is an exploded, perspective elevational view of the components of the prosthetic knee shown in FIGS. 2–4, with the femoral implant shown rotated 90° from the position in which it cooperates with the other components of the knee in order to better illustrate a cavity employed for constraining the components to each other.

Referring now specifically to FIGS. 2–5, the femoral implant has a somewhat U-shaped configuration, as is best seen in FIGS. 3 and 4, and is defined by a pair of spaced apart condyle sections 32 which are interconnected by and integrally constructed with a front plate 34 and which define between them a slot or recess 36 disposed beneath a housing 37 defined by a housing shell 39 which is integrally constructed with the condyle sections and an insert 41. The purpose for the housing is more fully discussed below. The side of the femoral implant facing the femur includes a spike 38 for insertion into an appropriately formed opening in the femur. Further, the femur facing sides include groove, depressions and the like, generally identified by reference numeral 40, for the retention of cement to facilitate the connection of the implant to the femur in the manner more fully described below.

The downwardly facing side of the femoral implant and, in particular of the condyle sections 32 define convex, compoundly curved condyle surfaces 42 which conform as closely as possible to the shape of the natural condyle surfaces. Thus, condyle surfaces 42 are complex surfaces with continuously changing radii of curvature so that sliding motions along the longitudinal extent of the condyle surfaces (shown in FIG. 3) duplicate the flexion-extension of a natural knee.

The femoral implant is preferably made of a biologically inert chromium-cobalt-molybdenum alloy and the condyle surfaces 42 are mirror polished to assure a low friction sliding interengagement with meniscal plate 30.

The meniscal plate is of a one-piece construction, preferably made from ultra-high molecular weight polyethylene. Its upwardly oriented face includes a pair of spaced apart, concave, compoundly curved depressions 44 that form bearing surfaces for the condyle surfaces 42 of the femoral implant. Disposed between the bearing surfaces is an upwardly extending protuberance 46 that is positioned and dimensioned so as to engage sides 48 of the condyle sections 32 which face recess 36. When the femoral implant 26 and the meniscus plate 30 are biased against each other so that condyle surfaces 42 rest in the spherical depressions 44, the protuberance 46 prevents substantially all relative movements between the femoral implant and the meniscal plate other than relative sliding motions between the two along the condyle surfaces, that is in the flexion-extension plane of the prosthetic and natural knee (Ref. no. 16 in FIGS. 1A and 1D).

The femoral implant and the meniscal plate are shaped so that sliding motion, which is essentially a pivotal motion as above described, can take place over the full pivotal range of the natural knee, e.g. through an arc of approximately 135°. Yet, substantially no relative motions in a lateral direction between the femoral implant and the meniscal plate are possible by virtue of the extension of protuberance 46 into recess 36.

The tibial implant 28 has a generally T-shaped configuration and is defined by a downwardly extending, tapered spike 50 and a plate member 52 which functionally replaces the natural tibial plateau of tibia 6. The spike is inclined relative to the plate member by an angle "α" of about 5° to 15°, and preferably of about 10°.

Alternatively the spike of the tibial implant may be replaced by a pair of spaced apart, downwardly depending generally parallel flanges (not shown) which are provided with holes and grooves for retaining filler material to cement the implant to the bone structure.

The plate member has a generally planar boundary and a generally rectangular plan configuration except for an arcuate cutout 56 along its aft boundary. The upwardly facing side of the plate member is defined by a concave, spherically shaped plateau surface 58 which has a radius of curvature "R". The origin 60 of the radius lies on the same side of the plate member as the femoral implant, i.e. it is "above" the plate member. Further, it lies on a center line which coincides with the lateral and longitudinal centers of the plate member as defined by its width "W" and depth "D" and which further is on or proximate the longitudinal axis of the prosthetic knee 24 when its components are fully extended (as illustrated in FIGS. 2 and 3). Further, the center line also coincides with the center line of spike 50 in the rear elevation as seen in FIG. 2.

As is the case with the femoral implant, the tibial implant 28 is of a uniform, i.e. one-piece construction, made of biologically inert, high strength metal such as the above-referenced chromium-cobalt-molybdenum alloy and the concave plateau surface 58 has a mirror polish to minimize friction during relative slidable movements of meniscal plate 30.

The underside 62 of the tibial implant has grooves or undercuts 64 to facilitate the bonding of the implant to surrounding bone structure. For a like purpose, spike 50 (as well as spike 38 of femoral implant 26) may be provided with longitudinally extending, cement receiving grooves 66.

The meniscal plate 30 has a plan configuration shaped complementary to that of plate member 52, that is it has a generally rectangular outline but it is of a slightly smaller size to allow it to move relative to the plate member without protruding past the boundary thereof. The meniscal plate has an undersurface 70 which is convex and spherically shaped and mates with the concave plateau surface of the tibial implant. The undersurface has the same radius of curvature "R". Although the undersurface is preferably a continuous surface, if desired, it can also be defined by two or more surface sections, separated by grooves, for example, so long as the surface section forms apart of a common spherical surface of a radius of curvature "R".

The prosthetic knee, as above described, provides the patient with substantially the same mobility as a natural knee. Flexion and extension of the knee takes place through corresponding slidable movements between condyle surfaces 42 and meniscal plate bearing surfaces 44. Flexion and extension is thus performed by surfaces which are a substantial duplicate of corresponding surfaces found in the natural knee. Accordingly, the condyle surfaces, particularly in regard to their longitudinal extent, that is in a direction parallel to plane 16 (see FIG. 1D) are formed so as to be identical to or correspond as closely as possible to the condyle surfaces of the natural knee.

During flexion and extension, the natural knee also goes through a certain amount of rotational motion. A corresponding motion takes place in the prosthetic knee of the present invention between the plateau surface 58 and the undersurface 70 of the meniscal plate. Similarly, relative sliding motion (in the third direction) or lateral abduction and adduction (in the fourth direction) are permitted by the prosthetic knee by virtue of corresponding sliding motions between the plateau surface and the undersurface of the meniscal plate.

It should be noted that at all times, substantially the full surface areas of the plateau surface 58 and of the undersurface 70 are in contact, thereby providing large contact areas and correspondingly small contact pressures. Further, compressive forces are substantially evenly distributed between the femur and the tibia over the full surface areas, forces are substantially evenly applied to both condyle surfaces 42 at all times, and the formation of forces which eccentrically act in the above summarized manner on either implant are avoided.

The prosthetic knee, as so far described, is ideally suited for implantation where the patient's ligaments are healthy. In such a case the ligaments maintain the components in mutual, stable engagement. However, if the ligaments are damaged, weakened, unduly stretched, or if they are non-existent the prosthetic knee, as so far described, does not provide a stable, movable connection between the patient's femur and tibia. To assure a stable connection under such circumstances the components of the prosthetic knee of the present invention are constrained to each other.

For this purpose a cylindrical post 72 is integrally constructed with tibial insert 28 and projects from the plateau surface 58 towards the femoral implant 26. A free end of the post has an enlarged diameter head 74 with an upper surface 76 that is convex and spherically shaped. The underside of the head defines a rim surface 78 which faces plateau surface 58 and which is oriented perpendicular to the cylindrical post. The rim surface extends over an arc of more than 180° and preferably no more than about 270°, and it is centered relative to the width "W" of the tibial plate member 52 for purposes more fully described hereinafter. The enlarged head 74 is cut back adjacent a forward end 80 of the post so as to define a pair of sloping surface sections 82 which are contiguous with ends of the rim surface, which face plateau surface 58, and which further slope away therefrom.

Meniscal plate 30 has a centrally located opening 84 of a diameter greater than the diameter of post head 74 so that the plate can be placed over and moved from the post and further so that the plate can move relative to the post (within the confines determined by the diameters of the post and of the opening) by sliding along the engaged plateau surface 58 and undersurface 70 of the meniscal plate.

The insert 41 of housing 37 carried by femoral implant 26 has a width (parallel to "W") which exceeds the diameter of post head 74, and it defines an interior cavity 86 of a width sufficient to receive therein the post head. The cavity terminates at opposing, spaced apart ledges 88 which project from lateral sides 90 of the cavity towards the cylindrical post to define surfaces which oppose and engage rim surface 78 of the post. A slot 92 extends from ledges 88 and communicates the cavity with the exterior. The slot has a width (in the direction of "W") slightly larger than the diameter of post 72.

Further, the insert has an exterior configuration which approximates the configuration of the aft portion of condyle surfaces 42; thus, the insert has a generally flat, downwardly facing side 94 and a contiguous upwardly and rearwardly facing side 96 through which the slot extends. The length of the slot is selected so that the forward end 80 of the post engages vertical (when the knee is fully extended) end surface 98 while the aft end 100 of the post is normally spaced from a generally upwardly inclined end surface 102 of the slot when the knee is fully flexed. The relative spacing and angular inclination of the slot ends are selected to permit flexion of the tibial implant relative to the femoral implant through the desired arc, normally through an arc of approximately 135°. Furthermore, the sloping surface sections 82 defined by cylindrical head 74 are shaped so that they slide and roll along ledges 88 when the implants are moved in the first direction without actually interfering with the smooth slidable movement as determined by the inter-engagement between condyle surfaces 42 and meniscal plate depressions 44.

The slot preferably also includes a slightly enlarged section midway between its ends 98 and 102 to facilitate the insertion and withdrawal of the enlarged post head 74. The width of the enclosed section is about equal to the width of the head portion between forward and aft post ends 80, 100, i.e., the width is greater than the width of the slot but less than the maximum transverse extent of the post head.

The post head is inserted in or withdrawn from the cavity by rotating the tibial implant 28 relative to the femoral implant 26 through approximately 90° about the axis of post 72 so that the forward and aft ends 80, 100 of the post face the sides of slot 92. The implants are then moved with respect to each other in the first direction until the post is approximately aligned with the enlarged slot section 104. Thereafter the post head can be withdrawn from or inserted in the cavity by pulling it from or pushing it toward the cavity with a slight rocking motion.

The insert itself is preferably constructed of a low friction material such as the above mentioned ultra-high molecular weight polyethylene. The outer configuration of the insert conforms to the interior shape of housing shell 39 and the insert is suitably secured to the shell as by bonding it thereto, forming a friction lock between them or the like.

Dimensionally, the tibial implant is sized to roughly correspond to the dimension of the tibial plateau of a natural knee. In a standard tibial implant, the plate member 52 of the tibial implant has a width "W" of 2.50", a depth "D" of 2.00", and a radius of curvature "R" for plateau surface 58 of 2.50" or more. This results in a maximum depth "T" for concavity formed by the plateau surface of about 3/16". A depth "T" in the range of about ⅛" to about 5/16" appears to be most desirable.

The meniscal plate 30 is similarly dimensioned although it is given a lesser width and depth so as to allow it to slide relative to the tibial implant along plateau surface 58. For a tibial plate member dimensioned as above set forth, the meniscal plate should have a width (parallel to "W") of no more than about 2.4" and a depth (parallel to "D") of no more than about 1.56". As for bearing surfaces 44 of the meniscal plate which receive condyle surfaces 42 of the femoral implant good results have been obtained by extending the depressions over substantially the full depth (in a direction parallel to "D") and compoundly curving the recesses with a transverse radius (in the direction of "W") of approximately 0.71", a longitudinal radius (parallel to "D") of 1.25" which results in a depth for the recess (measured from upwardly facing surface 45) of about ⅛ to 3/16".

As earlier mentioned, the spacing between plateau surface 58 and rim surface 78 exceeds the distance between the plateau surface and ledges 88 (when the implants 26, 28 and the meniscal plate 30 are in mutual contact) by no more than about 4 mm and preferably by no more than 2 mm. Thus, the patient's weight will normally bias the implants and the meniscal plate into firm engagement as is illustrated in FIG. 2A. However, under certain circumstances, and in conjunction with certain motions of the knee, the implants are permitted to expand relative to each other as is illustrated in FIG.

2B by up to the difference in the spacing between the rim surface and the ledges, respectively, and the plateau surface of the tibial implant.

The functioning of the prosthetic knee 24 of the present invention should now be apparent. After the respective implants have been implanted and are firmly attached to the patient's femur and tibia, the meniscal plate 30 is in place and enlarged head 74 of post 72 is disposed in housing cavity 86, the opposing rim surface 78 of the post and ledges 88 of the housing prevent an axial separation of the implants. Thus, the prosthetic knee of the present invention constrains its components to each other and thereby mechanically constrains the tibia to the femur.

Lateral stability between the implants and the meniscal plate is also assured by post 72 together with recess 48 between condyle sections 32 of the femoral implant and the cooperating, upwardly extending protuberance 46. It should be noted, however, that the slightly greater width of cavity slot 92 as compared to the diameter of post 72 permits slight lateral rocking motions in the fourth direction (abduction, adduction). Although such lateral motion is typically less than corresponding lateral motions permitted by a natural knee, the presence of such lateral mobility is highly desirable and assures a close approximation of the mobility of the natural knee. The absence of any lateral mobility as frequently encountered with constrained prior art knees and resulting stress problems at the cement-bone interface are thus avoided. Further, it should be noted that the implants are free to rotate with respect to each other about the axis of post 72. The knee surrounding, natural soft tissue, however, limits these movements in a gentle and relatively natural manner.

Flexion and extension between the implants 26, 28 takes place through corresponding sliding motion between condyle surfaces 42 and the concave depressions 44 of meniscal plate 30. As flexion-motion from the extended position of the knee (illustrated in FIG. 3) to the flexed position of the knee (illustrated in FIG. 4) takes place, the upwardly sloping surface sections 82 prevent an interference between ledges 88 and rim surface 78 which in turn would interfere with the smooth flexion-extension movement of the knee along the condyle surfaces. During such motion, the sloping surface sections remain proximate the ledges and thus continue to prevent the separation of the implants. At the same time, the end 98 of slot 92 limits extension motions by forming stops for post 72 at the terminal point of such movements to prevent a hyper-extension of the knee. Flexion is limited in a natural manner by the surrounding soft tissue. However, if desired for a particular application the other slot end 102 can be positioned to define a corresponding stop for post 72.

We claim:

1. A constrained prosthetic knee for implantation in a body comprising a femoral implant for connection to a femur defining a pair of spaced apart, convexly curved condyle sections; a meniscal plate having a pair of spaced apart, concavely curved bearing surfaces for cooperation with the condyle surfaces and permitting the latter to flex and extend relative to the former in a knee flexion-extension plane through a predetermined flexion-extension arc; a tibial implant for connection to the patient's tibia, the tibial implant including a plateau facing towards the femoral implant and having a concave, compoundly curved plateau surface; the meniscal plate further including a convex undersurface shaped complementarily to the plateau surface, the plateau surface and the undersurface having a shape permitting a substantially unrestrained relative sliding motion between the plateau surface and the undersurface when the plateau surface and the undersurface are biased against each other; and constraint means connected with the femoral implant and the tibial implant for preventing the separation of the implants and the meniscal plate, the constraint means permitting substantially unrestrained movement between the femoral implant and the meniscal plate in the flexion-extension plane over said arc and limiting the extent of relative sliding motions between the undersurface and the plateau surface.

2. A constrained prosthetic knee according to claim 1 including means preventing the femoral implant to extend relative to the tibial implant beyond a fully extended position.

3. A constrained prosthetic knee according to claim 2 wherein the means preventing movement comprises a post rigidly secured to the tibial implant and projecting from the plateau surface toward the femoral implant, slot means defined by the femoral implant positioned and oriented to receive the post and extending parallel to the flexion-extension plane, and at least one end wall of the slot means positioned to engage the post at an end of the flexion-extension arc to thereby prevent movement between the femoral implant and the meniscal plate beyond said arc.

4. A constrained prosthetic knee according to claim 1 wherein said flexion-extension arc approximately equals the flexion-extension arc through which a natural knee moves.

5. A constrained prosthetic knee according to claim 3 wherein said flexion-extension arc is approximately 135°.

6. A constrained prosthetic knee according to claim 1 wherein the undersurface and the plateau surface and convex and concave, respectively, and have a spherical shape with a substantially common radius of curvature and a common origin for the radius, and wherein the constraint means includes means permitting substantially unrestrained rotational sliding motion between the undersurface and the plateau surface about an axis intersecting said origin.

7. A constrained prosthetic knee according to claim 6 wherein the constraint means includes means limiting all relative sliding motions between the undersurface and the plateau surface other than said rotational motion to an arc about said origin of no more than a few degrees.

8. A constrained prosthetic knee according to claim 7 wherein the arc about said origin is less than five degrees.

9. A constrained prosthetic knee according to claim 8 wherein the arc about said origin is no more than about two degrees.

10. A constrained prosthetic knee according to claim 1 wherein the constraint means comprises a post means rigidly secured to the tibial implant and projecting from the plateau surface towards the femoral implant, the post means including means defining a rim surface facing the plateau surface, and holding means rigidly secured to the femoral implant and including a cavity shaped and positioned to receive a portion of the post means including the rim surface, the holding means including a ledge shaped, positioned and oriented so as to engage the rim surface to prevent a separation of the tibial implant and the femoral implant while permitting the substantially unrestrained movement between the femoral implant and the miniscal plate and limited relative sliding motions between the undersurface and the plateau surface.

11. A constrained prosthetic knee according to claim 10 wherein the post means includes a substantially cylindrical post which extends generally in the direction of the axis of the prosthetic knee when the latter is in its fully extended position; and wherein the rim surface is defined by a head portion of the post forming a free end thereof and extending at least partially beyond a periphery of the post.

12. A constrained prosthetic knee according to claim 11 wherein the head portion protrudes past the periphery of the post over an arc of the latter of more than 180 degrees.

13. A constrained prosthetic knee according to claim 12 wherein the rim surface is oriented substantially perpendicular to the post.

14. A constrained prosthetic knee according to claim 13 wherein the rim surface extends over an arc which is less than the arc over which the head portion extends.

15. A constrained prosthetic knee according to claim 14 wherein the rim surface extends over an arc of no more than 270 degrees.

16. A constrained prosthetic knee according to claim 15 wherein the head portion has a convex, compoundly curved surface facing away from the plateau surface.

17. A constrained prosthetic knee according to claim 10 wherein the meniscal plate includes a substantially centrally located hole, and wherein the post means extends through the hole past the meniscal plate when the undersurface contacts the plateau surface.

18. A constrained prosthetic knee according to claim 17 wherein the hole has a diameter greater than the diameter of the post means so as to enable the withdrawal of the post means from the hole.

19. A constrained prosthetic knee according to claim 10 wherein the holding means is disposed intermediate the condyle sections of the femoral implant.

20. A constrained prosthetic knee according to claim 19 wherein the femoral implant includes a housing disposed between the connected to the condyle sections, the cavity being disposed within the housing, and an elongated slot facing the plateau surface communicating the cavity with the exterior, dimensioned so as to receive therein the post means, and extending substantially parallel to the flexion-extension plane, the cavity having a sufficient size so as to freely receive therein the rim surface defining means, the cavity being further defined by opposing walls which are parallel to the flexion-extension plane, and wherein the ledge comprises first and second, parallel and spaced apart ledges which project from the walls toward a center of the cavity.

21. A constrained prosthetic knee according to claim 20 wherein the spacing between the plateau surface and the rim surface slightly exceeds the distance between the plateau surface and the ledge when the meniscal plate undersurface contacts the plateau surface and the condyle surfaces of the femoral implant engage the bearing surfaces of the meniscal plate so as to permit a limited separation between the implants in an axial direction.

22. A constrained prosthetic knee according to claim 21 wherein the spacing exceeds the distance by no more than about 4 mm.

23. A constrained prosthetic knee according to claim 22 wherein the spacing exceeds the distance by no more than about 2 mm.

24. A constrained prosthetic knee according to claim 20 wherein the post means comprise a generally cylindrical post projecting from the plateau surface toward the femoral implant and having an enlarged diameter head portion defining the rim surface, and wherein the head portion engages the opposing walls when the head portion is disposed within the cavity and the post extends through the slot.

25. A constrained prosthetic knee according to claim 24 wherein the slot is defined by opposing, elongate sides which extend substantially parallel to the cavity walls, the spacing between the sides being greater than a corresponding diameter of the post so as to permit limited relative rocking motions between the housing and the post and therewith between the femoral implant and the tibial implant in directions transverse to the direction of the condyle sections.

26. A constrained prosthetic knee according to claim 1 including means defined by the femoral implant and by the meniscal plate for limiting relative motions between them to relative motions in substantially the flexion-extension plane.

27. A constrained prosthetic knee according to claim 1 wherein the plateau surface has a substantially spherical shape.

28. A constrained prosthetic knee according to claim 27 wherein the concave plateau surface and the undersurface of the meniscal plate have a common center of curvature.

29. A constrained prosthetic knee comprising a femoral implant for connection to the femur of a patient defining a pair of generally parallel, spaced apart, convex, compoundly curved condyle surfaces and a housing therebetween; a tibial implant for connection to the tibia of the patient having a plate member oriented generally perpendicular to the tibia and including a concave, substantially spherically shaped plateau surface recessed into the member, and post means projecting substantially perpendicularly away from the plateau surface; a meniscal plate disposed between the implants, having a central hole through which the post means projects, a pair of concave bearing surfaces positioned and shaped to engage the condyle surfaces of the femoral implant, a protrusion extending into the recess for limiting relative motion between the femoral implant and the meniscal plate to motions corresponding to flexion and extension motions of the patient's natural knee, and a convex undersurface for engaging the plateau surface, portions of the undersurface engaging the plateau surface having a substantially spherical shape and the same radius of curvature as the plateau surface of the tibial implant whereby the undersurface can freely slidably rotate relative to the plateau surface about the post means while other relative sliding motion between the undersurface and the plateau surface are limited to the difference between the size of the hole and the size of the post means; the housing of the femoral implant defining a cavity and a slot communicating the cavity with the exterior, the slot facing the plateau surface and the post means extending through the slot into the cavity, the slot having an extent in the direction of flexion and extension movements between the condyle surfaces and the bearing surfaces so that a free end of the post means is at all times disposed in the cavity while relative flexion and extension movements between the femoral implant and the meniscal plate take place; the housing and the post means further defining constraint means for preventing the separation of the implants in an axial direction, permitting substantially unrestrained rotational movements between the post means and the femoral implant about an axis of the post means, and for further permitting said limited relative motion between the post means and the housing in directions transverse to the flexion and extension movements.

30. A constrained prosthetic knee according to claim 29 wherein an exterior of the housing facing in the direction in which the condyle surfaces face extends in generally the same direction as the condyle surfaces, and wherein the slot is an elongate slot having a width slightly greater than a corresponding transverse dimension of the post means and a longitudinal extent so that the post means can move relative to the housing through the same arc through which the condyle surfaces can move relative to the bearing surfaces for flexion and extension movements of the prosthetic knee.

31. A constrained prosthetic knee according to claim 29 wherein the constraint means comprises first and second, spaced apart retaining ledges defined by the housing and disposed within the cavity, the ledges facing in a direction opposite to the condyle surfaces and being oriented substantially perpendicular to the post means when the prosthetic knee is in its extended position; and an enlarged head portion forming a free end of the post means, the head portion including a rim surface facing the plateau surface and oriented substantially perpendicular to the post means for engaging the ledge and thereby constraining the post means to the housing.

32. A constrained prosthetic knee according to claim 31 wherein the rim surface extends over an arc of less than 360° and is positioned relative to the post means so that the rim surface can simultaneously contact the ledges, and wherein the head portion further defines a curved surface section which is contiguous with the rim surface and which slopes from the rim surface along the post means away from the plateau surface so as to permit relative flexion and extension movements between the implants and therewith between the post means and the housing while the curved surface section continues to engage the ledges and thereby continues to constrain the implants to each other.

33. A constrained prosthetic knee according to claim 32 wherein the slot has a width slightly greater than a corresponding transverse dimension of the post so as to enable relative movement of the post while the head portion is disposed within the cavity.

34. A constrained prosthetic knee according to claim 33 wherein the slot has a section intermediate its end which has an enlarged width, the slot section extending from the cavity to the exterior to facilitate the withdrawal of the head portion from the cavity along the slot section.

35. A constrained prosthetic knee according to claim 34 wherein the slot ends are positioned to engage the post means at terminal points of the flexion-extension movement between the femoral implant and the tibial plate to thereby limit the arc over which such movement can take place.

36. A constrained prosthetic knee according to claim 29 wherein the housing includes a housing shell that is integrally constructed with portions of the femoral implant defining the condyle surfaces, and an insert received by the shell and secured thereto which defines the cavity and the slot.

37. A constrained prosthetic knee according to claim 36 wherein the implants are constructed of a metal, and wherein the insert is constructed of a plastic material.

38. A constrained prosthetic knee according to claim 29 wherein the constraint means includes means permitting relative movement between the implants in an axial direction of no more than about 4 mm.

39. A constrained prosthetic knee according to claim 38 wherein the constraint means is defined by cooperating, oppositely positioned and overlapping surfaces defined in the cavity of the housing and on a free end of the post means, the spacing between the plateau surface and the overlapping surface on the post means exceeding the distance between the plateau surface and the corresponding overlapping surface in the cavity by a few mm.

40. A constrained prosthetic knee for implantation in a body comprising a femoral implant for connection to a femur defining a pair of spaced apart, convexly curved condvle sections; a meniscal plate having a pair of spaced apart, concavely curved bearing surfaces for cooperation with the condyle surfaces and permitting the latter to flex and extend relative to the former in a knee flexion-extension plane through a predetermined flexion-extension arc; a tibial implant for connection to the patient's tibia, the tibial implant including a plateau facing towards the femoral implant and having a plateau surface; the meniscal plate further including an undersurface shaped complementarily to the plateau surface to permit sliding motion between the plateau surface and the undersurface when the plateau surface and the undersurface are biased against each other; and constraint means connected with the femoral implant and the tibial implant for preventing the separation of the implants and the meniscal plate, the constraint means including a substantially cylindrical post rigidly secured to the tibial implant and projecting from the plateau surface towards the femoral implant generally in the direction of the axis of the prosthetic knee when the latter is in its fully extended position, the post including a head portion forming a free end of the post, and protruding past the periphery of the post over an arc of the latter of more than 180° to define a rim surface oriented substantially perpendicular to the post and facing the plateau surface, and extending over an arc which is less than the arc over which the head portion extends, and holding means rigidly secured to the femoral implant and including a cavity shaped and positioned to receive the head portion including the rim surface, the holding means including a ledge shaped, positioned and oriented so as to engage the rim surface to prevent a separation of the tibial implant and the femoral implant while permitting substantially unrestrained movement between the femoral implant and the meniscal plate and relative sliding motions between the undersurface and the plateau surface.

41. A constrained prosthetic knee according to claim 40 wherein the rim surface extends over an arc of no more than 270°.

42. A constrained prosthetic knee according to claim 41 wherein the head portion has a convex, compoundly curved surface facing away from the plateau surface.

43. A constrained prosthetic knee for implantation in a body comprising a femoral implant for connection to a femur defining a pair of spaced apart, convexly curved condyle sections; a meniscal plate having a pair of spaced apart, concavely curved bearing surfaces for cooperation with the condyle surfaces and permitting the latter to flex and extend relative to the former in a knee flexion-extension plane through a predetermined flexion-extension arc; a tibial implant for connection to the patient's tibia, the tibial implant including a plateau facing towards the femoral implant and having a plateau surface; the meniscal plate further including an undersurface shaped complementarily to the plateau surface to permit relative sliding motion between the plateau surface and the undersurface when the plateau surface and the undersurface are biased against each other; and contraint means connected with the femoral implant and the tibial implant for preventing the separation of the implants and the meniscal plate, the constraint means including post means rigidly secured to the tibial implant and projecting from the plateau surface towards the femoral implant, the post means including means defining a rim surface facing the plateau surface, a housing defined by the femoral implant, disposed between and connected to the condyle sections, and defining a cavity shaped and positioned and having a sufficient size so as to freely receive therein the rim surface defining means, the cavity being further defined by opposing walls which are parallel to the flexion-extension plane, and wherein the ledge comprises first and second, parallel and spaced apart ledges which project from the walls toward a center of the cavity, the femoral implant including an elongated slot facing the plateau surface communicating the cavity with the exterior, dimensioned so as to receive therein the post means, and extending substantially parallel to the flexion-extension plane, whereby the ledge engages the rim surface and thereby prevents a separation of the tibial implant and the femoral implant while permitting the substantially unrestrained movement between the femoral implant and the meniscal plate and relative sliding motions between the undersurface and the plateau surface.

44. A constrained prosthetic knee according to claim 43 wherein the spacing between the plateau surface and the rim surface slightly exceeds the distance between the plateau surface and the ledge when the meniscal plate undersurface contacts the plateau surface and the condyle surfaces of the femoral implant engage the bearing surfaces of the meniscal plate so as to permit a limited separation between the implants in an axial direction.

45. A constrained prosthetic knee according to claim 44 wherein the spacing exceeds the distance by no more than about 4 mm.

46. A constrained prosthetic knee according to claim 45 wherein the spacing exceeds the distance by no more than about 2 mm.

47. A constrained prosthetic knee according to claim 43 wherein the post means comprises a generally cylindrical post projecting from the plateau surface toward the femoral implant and having an enlarged diameter head portion defining the rim surface, and wherein the head portion engages the opposing walls when the head portion is disposed within the cavity and the post extends through the slot.

48. A constrained prosthetic knee according to claim 47 wherein the slot is defined by opposing, elongate sides which extend substantially parallel to the cavity walls, the spacing between the sides being greater than a corresponding diameter of the post so as to permit limited relative rocking motions between the housing and the post and therewith between the femoral implant and the tibial implant in directions transverse to the direction of the condyle sections.

49. A constrained prosthetic knee comprising a femoral implant for connection to the femur of a patient defining a pair of generally parallel, spaced apart convex, compoundly curved condyle surfaces and a housing therebetween; a tibial implant for connection to the tibia of the patient having a plate member oriented generally perpendicular to the tibia and defining a plateau surface, and post means projecting substantially perpendicularly away from the plateau surface; a meniscal plate disposed between the implants, having a central hole through which the post means projects, a pair of concave bearing surfaces positioned and shaped to engage the condyle surfaces of the femoral implant, a protrusion extending into the recess for limiting relative motion between the femoral implant and the meniscal plate to motions correspoinding to flexion and extension motions of the patient's natural knee, and an undersurface for engaging the plateau surface, the undersurface and the plateau surface being shaped so that the undersurface can freely slidably rotate relative to the plateau surface about the post means while other relative sliding motion between the undersurface and the plateau surface are limited to the difference between the size of the hole and size of the post means; the housing of the femoral implant defining a cavity and a slot communicating the cavity with the exterior, the slot facing the plateau surface and the post means extending through the slot into the cavity, the slot having an extent in the direction of flexion and extension movements between the condyle surfaces and the bearing surfaces so that a free end of the post means is at all times disposed in the cavity while relative flexion and extension movements between the femoral implant and the meniscal plate take place; the housing and the post means further defining constraint means for preventing the separation of the implants in an axial direction, for permitting substantially unrestrained rotational movements between the post means and the femoral implant about an axis of the post means, and for further permitting said limited relative sliding motion between the post means and the housing in directions transverse to the flexion and extension movements, the constraint means comprising first and second, spaced apart retaining ledges defined by the housing and disposed within the cavity, the ledges facing in a direction opposite to the condyle surfaces and being oriented substantially perpendicular to the post means when the prosthetic knee is in its extended position; and an enlarged head portion forming a free end of the post means, the head portion including a rim surface facing the plateau surface and oriented substantially perpendicular to the post means for engaging the ledges and thereby constraining the post means to the housing, the rim surface extending over an arc of less than 360° and being positioned relative to the post means so that the rim surface can simultaneously contact the ledges, and wherein the head portion further defines a curved surface section which is contiguous with the rim surface and which slopes from the rim surface along the post means away from the plateau surface so as to permit relative flexion and extension movements between the implants and therewith between the post means and the housing while the curved surface section continues to engage the ledges and thereby continues to constrain the implants to each other.

50. A constrained prosthetic knee according to claim 49 wherein the slot has a width slightly greater than a corresponding transverse dimension of the post so as to enable relative movement of the post while the head portion is disposed within the cavity.

51. A constrained prosthetic knee according to claim 50 wherein the slot has a section intermediate its end which has an enlarged width, the slot section extending from the cavity to the exterior to facilitate the withdrawal of the head portion from the cavity along the slot section.

52. A constrained prosthetic knee according to claim 51 wherein the slot ends are positioned to engage the post means at terminal points of the flexion-extension movement between the femoral implant and the tibial plate to thereby limit the arc over which such movement can take place.

* * * * *